United States Patent [19]
Graham

[11] Patent Number: 5,322,609
[45] Date of Patent: Jun. 21, 1994

[54] DEVICE FOR DETECTING ELECTROLYTES IN LIQUID SAMPLES

[75] Inventor: Steven P. Graham, Parkton, Md.

[73] Assignee: Becton, Dickinson and Company, Franklin Lakes, N.J.

[21] Appl. No.: 950,614

[22] Filed: Sep. 24, 1992

[51] Int. Cl.$^5$ .......................................... G01N 27/26
[52] U.S. Cl. .................. 204/403; 204/416; 204/422; 204/423; 435/817
[58] Field of Search ............ 204/403, 422, 423, 416; 128/635, 637, 639, 763, 770, 632; 435/817

[56] References Cited

U.S. PATENT DOCUMENTS

| | | | |
|---|---|---|---|
| 3,878,830 | 4/1975 | Bicher | 128/635 |
| 4,016,866 | 4/1977 | Lawton | 128/635 |
| 4,159,234 | 6/1979 | Eifler | 204/428 |
| 4,841,974 | 6/1989 | Gumbrecht et al. | 204/403 |
| 4,927,502 | 5/1990 | Reading et al. | 204/403 |

Primary Examiner—John Niebling
Assistant Examiner—Bruce F. Bell
Attorney, Agent, or Firm—Richard J. Rodrick

[57] ABSTRACT

A biosensor device for detecting electrolytes in liquid samples includes a capillary tube having a lumen extending therethrough. This lumen receives and retains liquid to be sampled for electrolytes. A tube holder is engaged at one end of the tube. This tube holder includes a bore therethrough in fluid communication with the lumen of the tube. A biosensor is positioned within the lumen of the tube. The biosensor is capable of generating an electrical signal responsive to the presence of one or more electrolytes in the liquid sample. Electrical contact elements are associated with the biosensor for measuring the electrical signal for the detection of electrolytes in the sample.

10 Claims, 3 Drawing Sheets

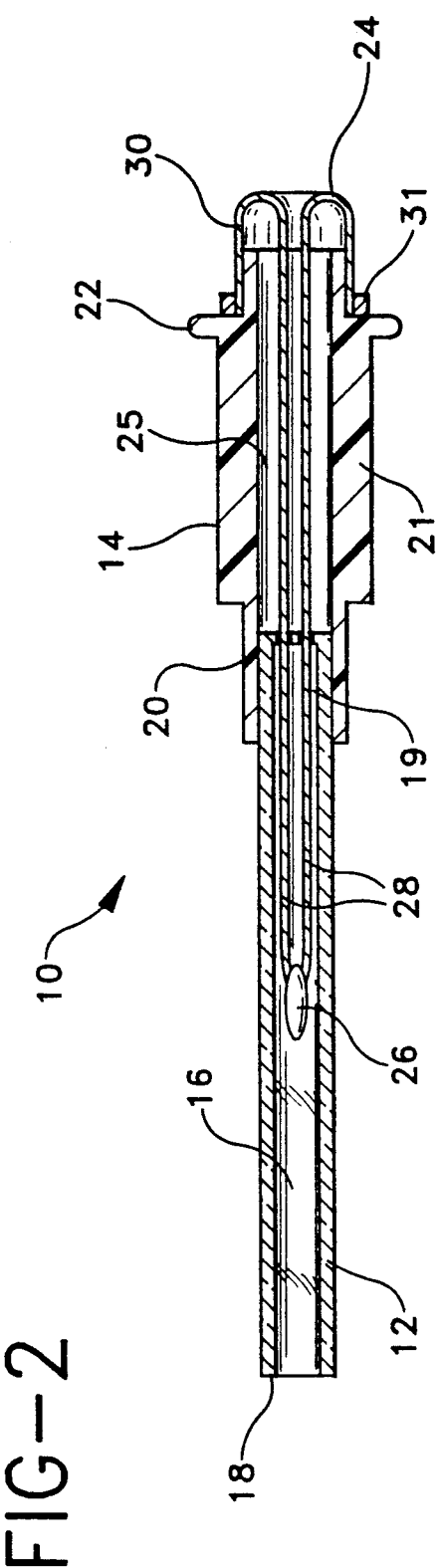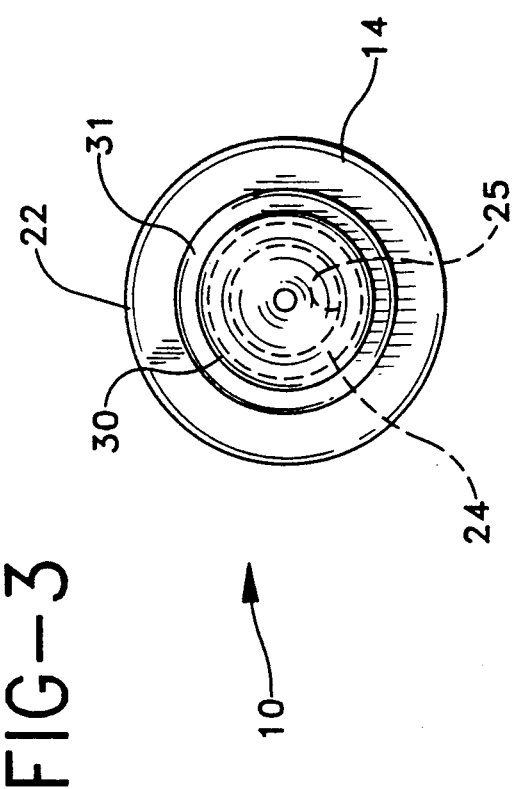

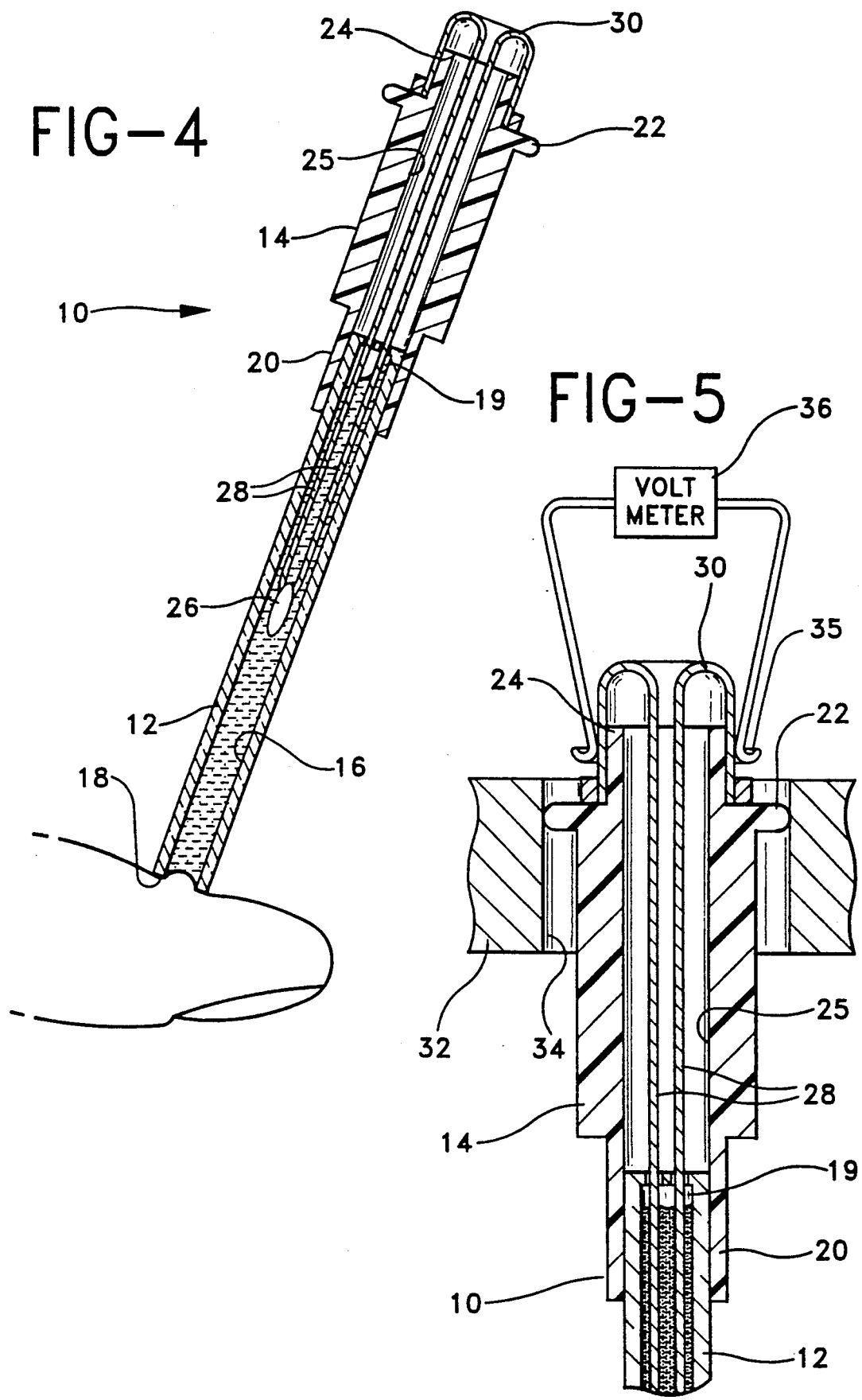

DEVICE FOR DETECTING ELECTROLYTES IN LIQUID SAMPLES

BACKGROUND OF THE INVENTION

1. Field of the Invention

The present invention relates to a device for detecting electrolytes in liquid samples, and more particularly, concerns a biosensor device for detecting one or more electrolytes in a blood sample.

2. Background Description

In the testing of body fluid samples, such as blood, it is common to make an analysis for the presence of electrolytes, including sodium, potassium and calcium ions. In a typical procedure for obtaining blood from a patient, the patient's blood vessel is penetrated by a needle and the blood sample is collected into an evacuated blood collection tube. This tube is then sent to a laboratory for a number of tests, including the tests for the presence and concentration of electrolytes.

While these procedures for obtaining blood samples are easily practiced and well accepted, it is nevertheless desirable to make improvements which would benefit not only the patient but also the medical personnel who carry out these procedures and necessarily must handle the blood sample. For example, instead of obtaining blood from a peripheral blood vessel by use of a needle, a less invasive approach would be desirable. Further, a minimal amount of blood required for electrolyte analysis should be taken from the patient. The patient would not only be pleased with the approach, but those medical personnel charged with handling blood samples would not have to deal with excess quantities of blood. Also, simple blood testing equipment, for detecting the presence or concentration of analytes, is desired. This would keep down expense and complexity. It would also be desirable to have the blood sample presented to the detection device as soon as possible after collection from the patient. This would prevent any deterioration in the blood sample which may occur if there is a long time between collection from the patient and actual analysis at the lab.

The present invention seeks to achieve the foregoing and other improvements in the detection of electrolytes in liquid samples, such as blood.

SUMMARY OF THE INVENTION

The biosensor device of the present invention for detecting electrolytes in liquid samples comprises a tube having a lumen therethrough. Liquid to be sampled for electrolytes is received and retained in the lumen. A tube holder is engaged at one end of the tube. This holder includes a bore therethrough in fluid communication with the lumen of the tube. A biosensor is positioned within the lumen of the tube. The biosensor is capable of generating an electrical signal responsive to the presence of one or more electrolytes in the liquid sample. There are means associated with the biosensor for measuring the electrical signal for the detection of electrolytes in the sample.

In accordance with the principles of the present invention, the biosensor device provides the improvements set forth above. In particular, the device is simple and straightforward to use and is disposable and inexpensive. Its use requires minimal exposure to blood, since capillary blood may be used for sampling. In a single device, the liquid sample may be collected, presented to a biosensor for electrolyte detection purposes, and then the device, containing the liquid sample, may be electrically connected to a measuring instrument for the detection of electrolytes in the sample. If a shield is employed for the tube, it may be replaced over the contaminated end of the tube after use.

BRIEF DESCRIPTION OF THE DRAWINGS

FIG. 2 is a cross sectional view of the device taken along line 2—2 of FIG. 1;

FIG. 3 is an end view of the holder end of the device of FIG. 1;

FIG. 4 is a cross sectional view of the device schematically illustrating obtaining a blood sample from a patient's finger; and FIG. 5 is a partial cross sectional view of the device schematically illustrating its connection in a measuring instrument and an electrical contact for making electrical measurements.

DETAILED DESCRIPTION

Figure 1:
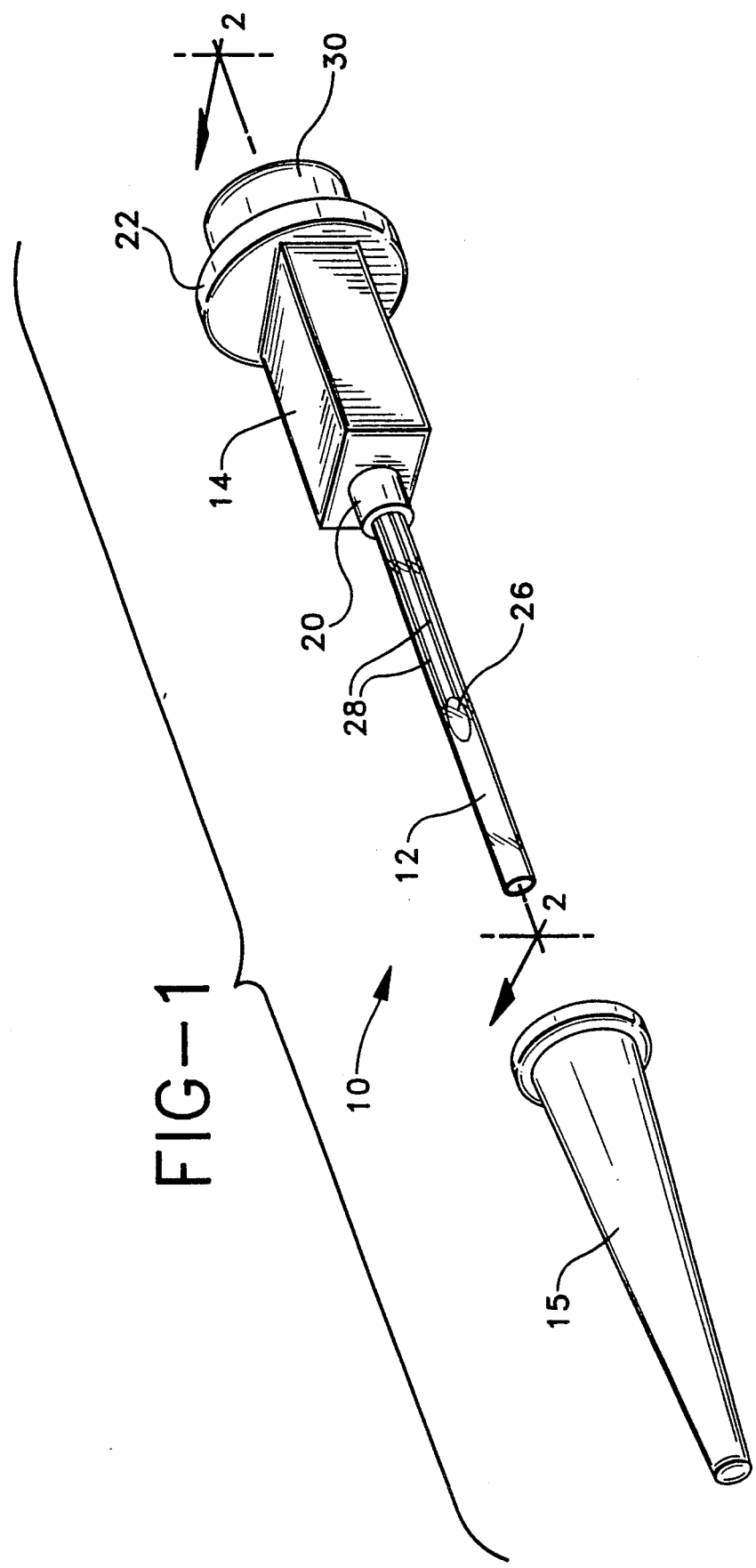
FIG. 1 an exploded perspective view of the preferred embodiment of the biosensor device of the present invention.

While this invention is satisfied by embodiments in many different forms there is shown in the drawings and will herein be described in detailed a preferred embodiment of the invention, with the understanding that the present disclosure is to be considered as exemplary of the principles of the invention and is not intended to limit the invention to the embodiment illustrated. The scope of the claims will be measured by the appended claims and their equivalents.

Referring to the drawings, and FIG. 1 in particular, the preferred biosensor device 10 of the present invention is illustrated. This biosensor device includes a hollow tube 12 and a holder 14 at one end of the tube. In addition, the biosensor device may include a shield 15 which is positioned over and covers tube 12. Shield 15 is readily removable for use of the device, and the shield may be replaced over the tube after it has been filled with liquid for sampling, if desired, to protect the user from the contaminated end of the tube.

Turning now to FIG. 2, it can be seen that tube 12 includes a lumen 16 extending completely therethrough, the lumen terminating in an open end 18 at one end of the tube and an open end 19 at the other end of the tube. This hollow tube is preferably an elongate, small bore capillary tube or pipette. Capillary tubes are well known as used in the collection of small quantity blood samples from patients. Due to the slender, elongate nature of capillary tubes, blood or other liquid samples may be readily drawn into the lumen of the tubes, and the liquid is retained therein by virtue of capillary surface tension. It is preferred that tube 12 be made of clear material, such as glass or plastic, although other materials may be used. Typically, the volume of liquid that tube 12 may hold ranges from 25 $\mu l$ to 50 $\mu l$ when the liquid to be sampled is blood.

Tube holder 14 includes a collar 20 into which one end of tube 12 is engaged. The tube may be attached to the collar by any suitable means, including adhesives, interference fit, and the like. Tube holder 14 also includes a body portion 21 and a finger flange 22, both elements of which allow the user to readily grasp the device for use. Also, body portion 21 and flange 22 serve as a plug element for introduction of a device into a measurement instrument, as will be described below.

Projecting away from flange 22 is a raised rim 24. Extending completely through holder 14 is a bore 25, which is in fluid communication with lumen 16 of the tube. It is preferred that holder 14 be made from an electrically non conductive material, such as plastic, ceramic or the like.

Positioned within lumen 16 of the tube is a biosensor element 26. The biosensor is typically a tiny device capable of generating an electrical signal in the presence of an electrolyte in the liquid sample. For example, the biosensor may detect potassium, sodium, calcium and other ions present in a . blood sample. This type of biosensor device is small enough to fit within the slender lumen of the capillary tube, since typically the thickness of such a device is that of a human hair. Such a biosensor device is described in, or available from Applied Biosensor, Inc., Flanders, N.J. A typical biosensor of the type described is capable of producing electrical signals in the magnitude of millivolts. By detecting these electrical signals with a sensitive reader or instrument, the presence or concentration of the electrolytes in the liquid sample can be established.

In order to access the electrical signals from biosensor element 26, electrically conductive leads 28 extend from the biosensor. These leads are preferably sufficiently stiff or rigid so that biosensor element 26, at one end of the leads, may be suspended within lumen 16 of the capillary tube. The positioning of biosensor element 26 is generally not critical, but it is preferred that the biosensor be located about midway along the length of the tube.

Leads 28 extend through lumen 16 and bore 25 and emerge from one end of holder 14. The ends 30 of the electrical leads form a cap or rim 24 at the end of holder 14, and are secured in place by a ring 31. In this particular embodiment, the electrical leads are thus exposed for an external electrical connection by an appropriate electrical contact, as described below.

FIG. 4 illustrates the use of the biosensor device in obtaining a blood sample from the finger of a patient. Prior to the use of the present device, a small amount of blood is caused to flow from the patient's finger by use of a lancet or similar device, commonly used for these procedures. Then, open end 18 of capillary tube 12 is placed against the patient's finger with the exposed blood, and blood flows into lumen 16 by capillary action. Sufficient blood is drawn into lumen 16 so that biosensor element 26 is completely immersed within the blood sample. Once this blood sample is collected, it is normally retained within the capillary tube without dripping out, due to the surface tension forces. At this time, shield 15 may be replaced over tube 12, if desired, in order to prevent any contact from the contaminated end of the capillary tube.

To analyze this liquid sample obtained in the biosensor device, the device may be introduced into an appropriate reader or instrument for measuring electrical signals generated by the biosensor element. As seen in FIG. 5, such an instrument 32 is schematically illustrated. Holder 14 may fit, in plug-like fashion, in an appropriate aperture 34 within the instrument. With the holder plugged into this aperture, the ends 30 of the electrical leads are exposed. Electrical contacts 35, as part of an electrical connection mechanism, are caused to engage the ends of the electrical leads, as seen in FIG. 5. A voltmeter 36, or any other appropriate measuring device, whether analogue or digital, may be connected to contact elements 35 in order to detect any electrical signal conducted by the leads from biosensor element 26. In this way, the presence or concentration of electrolytes in the liquid sample may be detected.

Thus, the present invention provides a simple and straightforward analyzer for electrolytes in liquid samples. By use of a tiny biosensor element, it is possible to analyze very small samples of blood for electrolytes. Further, the present invention provides for the collection of the blood sample, the presentation of blood to a biosensor element and the electrical connection of the biosensor element to a measurement instrument all in one device and all within a short period of time.

What is claimed is:

1. A biosensor device for detecting electrolytes in liquid samples into vitro comprising:
   a tube having a lumen therethrough for the receipt and retention of liquid to be sampled for electrolytes;
   a tube holder engaged at one end of the tube, said holder including a bore therethrough in fluid communication with the lumen of said tube;
   an electrolyte-responsive biosensor positioned within the lumen of said tube at a location to be contacted in vitro by the liquid to be sampled, which generates an electrical signal responsive to the presence of one or more electrolytes in the liquid sample; and
   means associated with said biosensor for measuring said electrical signal for the detection of electrolytes in the sample.

2. The device of claim 1 wherein the tube is a capillary tube.

3. The device of claim 1 wherein the holder is made from electrically non-conductive material.

4. The device of claim 1 wherein the biosensor produces millivolt signals when contacted by an electrolyte in the sample.

5. The device of claim 4 wherein the biosensor produces electrical signals responsive to the presence of sodium and potassium ions in the liquid sample.

6. The device of claim 1 wherein the means for measuring includes electrically conductive leads associated with said biosensor and extending through the bore of said holder for making an electrical contact thereto.

7. The device of claim 6 wherein said leads are secured to an external surface of the holder to facilitate making an electrical contact thereto by a separate measuring instrument.

8. The device of claim 1 which further includes a shield removably positioned over said tube.

9. The device of claim 1 wherein the biosensor produces an electrical signal responsive to the presence of one or more electrolytes in a sample of blood.

10. The device of claim 9 wherein the biosensor is positioned in said lumen to be completely immersed when blood is introduced into said lumen.

* * * * *